United States Patent

Buhr et al.

[11] Patent Number: 5,563,018
[45] Date of Patent: Oct. 8, 1996

[54] (1,2-NAPHTHOQUINONE 2-DIAZIDE) SULFONIC ACID ESTERS, RADIATION-SENSITIVE MIXTURE PREPARED THEREWITH AND RADIATION-SENSITIVE RECORDING MATERIAL

[75] Inventors: Gerhard Buhr, Koenigstein; Wolfgang Zahn; Fritz Erdmann, both of Eltville; Siegfried Scheler, Wiesbaden, all of Germany

[73] Assignee: Hoechst Aktiengesellschaft, Frankfurt am Main, Germany

[21] Appl. No.: 32,276

[22] Filed: Mar. 17, 1993

[30] Foreign Application Priority Data

Mar. 23, 1992 [DE] Germany .......................... 42 09 343.0

[51] Int. Cl.⁶ ........................................ G03F 7/023
[52] U.S. Cl. ........................ 430/192; 430/165; 430/193; 534/557
[58] Field of Search .................... 430/192, 193, 430/165; 534/557

[56] References Cited

U.S. PATENT DOCUMENTS

| 4,424,270 | 1/1984 | Erdmann et al. | 430/166 |
|---|---|---|---|
| 4,555,469 | 11/1985 | Erdmann et al. | 430/168 |
| 4,863,827 | 9/1989 | Jain et al. | 430/191 |
| 4,929,536 | 5/1990 | Spak et al. | 430/193 |
| 4,931,381 | 6/1990 | Spak et al. | 430/165 |
| 5,114,816 | 5/1992 | Scheler et al. | 430/192 |
| 5,217,840 | 6/1993 | Spak et al. | 430/165 |
| 5,238,775 | 8/1993 | Kajita et al. | 430/192 |

FOREIGN PATENT DOCUMENTS

| 0336605 | 10/1989 | European Pat. Off. . |
| 0351849 | 1/1990 | European Pat. Off. . |
| 1-017049 | 1/1989 | Japan . |

OTHER PUBLICATIONS

Münzel et al., "A–and B– Parameter Dependent Submicron Stepper Performance of Positive Tupe Photoresist," *Microelectronic Engineering*, vol. 6, pp. 421–426 (1987).

Trefonas et al., "New Principle for Image Enhancement in Single Layer Positive Photoresists," *SPIE*, vol. 771, pp. 194–210 (1987).

Kosar, *Light Sensitive Systems: Chemistry and Application of Nonsilver Halide Photographic Processes*, (New York: John Wiley & Sons, Inc.), pp. 336–353 (1965).

*Primary Examiner*—John S. Y. Chu
*Attorney, Agent, or Firm*—Foley & Lardner

[57] ABSTRACT

The invention relates to 2,3,4-trihydroxy-3'-methyl-, -ethyl-, -propyl- or -isopropylbenzophenone which is completely esterified with (1,2-naphthoquinone 2-diazide)-4-sulfonic acid and/or (7-methoxy-1,2-naphthoquinone 2-diazide)-4-sulfonic acid, a radiation-sensitive mixture prepared therewith, and a radiation-sensitive recording material comprising a substrate and a radiation-sensitive layer which is composed of the mixture according to the invention.

15 Claims, No Drawings

(1,2-NAPHTHOQUINONE 2-DIAZIDE) SULFONIC ACID ESTERS, RADIATION-SENSITIVE MIXTURE PREPARED THEREWITH AND RADIATION-SENSITIVE RECORDING MATERIAL

BACKGROUND OF THE INVENTION

1. Field of the Invention

The invention relates to novel (1,2-naphthoquinone 2-diazide)sulfonic acid esters of substituted trihydroxybenzophenones and a radiation-sensitive mixture prepared therewith.

The invention also relates to a radiation-sensitive recording material comprising a substrate and a radiation-sensitive layer.

2. Description of Related Art

An important step in the production of electronic components is the imagewise irradiation and subsequent development of a radiation-sensitive layer which has been applied to the material to be patterned. Such a layer may be positive- or negative-working.

In a positive-working layer, photoactive components are generally used which contain (1,2-naphthoquinone 2-diazide) units. A large number of such components, primarily esters of aromatic polyhydroxy compounds and (1,2-naphthoquinone 2-diazide)sulfonic acid are described in the book by Jaromir Kosar: *Light-Sensitive Systems*, John Wiley + Sons, New York, 1965, pp. 343–351.

Progressive miniaturization in the production of electronic components requires the generation of ever smaller patterns. This necessitates radiation-sensitive photoresists having ever higher resolving power. It is known that the resolution is improved by increasing the content of diazoquinone in the radiation-sensitive layer. See H. Münzel, J. Lux, R. Schulz, "A- and B-Parameter dependent Submicron Stepper Performance of Positive Type Photoresist," *Microelectronic Engineering*, 6: 421–426, 1987. P. Trefonas III and B. K. Daniels, "New Principle for Image Enhancement in Single Layer Positive Photoresists" *Proceedings of SPIE*, 771:194–210 (1987), 194–210, points out that compounds containing a plurality of diazonaphthoquinone units achieve higher contrasts and consequently a better resolution.

Frequently used compounds containing a plurality of diazonaphthoquinone units which are often described in patent literature are esters of (1,2-naphthoquinone 2-diazide)-4- and -5-sulfonic acid and polyhydroxybenzophenone, the 2,3,4-trihydroxybenzophenone being preferred among the polyhydroxybenzophenones.

A disadvantage of these esters is, however, their relatively low solubility in the solvents generally used, it not being possible, consequently, to increase their concentration in the radiation-sensitive mixtures to the desired extent. A further increase in the resolving power is therefore not possible by this method. In addition, the resist mixtures prepared with these esters do not have adequate shelf life.

These disadvantages were already known and have been described in JP-A 01-017049. This document discloses improving the shelf life of the resists by using esters of (1,2-naphthoquinone 2-diazide)-5-sulfonic acid and 2,3,4-trihydroxy-2'-methylbenzophenone.

SUMMARY OF THE INVENTION

The object of the present invention is therefore to provide esters of (1,2-naphthoquinone 2-diazide)sulfonic acid and a 2,3,4-trihydroxybenzophenone, which esters have improved solubility in the solvents used for photoresists, can readily be prepared in chemically homogeneous form and do not adversely affect the lithographic properties of the radiation-sensitive mixtures. In addition, the use of the novel naphthoquinone diazides is intended to markedly improve the shelf life of the resists. Furthermore, the novel naphthoquinone diazides are not intended to significantly affect the absorption properties of the resists.

It is also an object of the present invention to provide a radiation-sensitive mixture containing such an improved ester and to provide a radiation-sensitive recording material containing such a mixture.

In accordance with the foregoing objects of the present invention, there is provided a 2,3,4-trihydroxy-3'-methyl-, -ethyl-, -propyl- or -isopropylbenzophenone which is completely esterified with at least one of (1,2-naphthoquinone 2-diazide)-4-sulfonic acid and (7-methoxy- 1,2-naphthoquinone 2-diazide)-4-sulfonic acid.

In accordance with another aspect of the present invention there has been provided a radiation-sensitive mixture comprising a polymeric, water-insoluble binder which is soluble, or at least swellable, in organic solvents and aqueous alkaline solutions; and at least one radiation-sensitive compound as described above.

In accordance with another aspect of the present invention, there has been provided a radiation-sensitive recording material comprising a substrate and a radiation-sensitive layer, wherein the layer comprises a radiation-sensitive mixture as described above.

In accordance with another aspect of the present invention, there has been provided a method of making a radiation-sensitive recording material.

Further objects, features, and advantages of the present invention will become apparent from the detailed description of preferred embodiments which follows.

DETAILED DESCRIPTION OF PREFERRED EMBODIMENTS

It is surprising that the object of the invention can be achieved with the esters described above, because JP-A 01-017049 states that 3'-methyl-2,3,4-trihydroxybenzophenone completely esterified with (1,2-naphthoquinone 2-diazide)-5-sulfonic acid results in resist formulations having inadequate shelf life.

In the present invention, the 2,3,4-trihydroxy-3'-methyl, -ethyl, -propyl, or -isopropyl benzophenone may be esterified completely with either of the sulfonic acids or a mixture thereof having any desired proportion of the sulfonic acids.

Of the compounds according to the invention, the esters of 3'-methyl-2,3,4-trihydroxybenzophenone are preferred.

The compounds according to the invention may be prepared by any desired process, such as processes generally known per se to the person skilled in the art. For example, the 3'-alkyl-substituted 2,3,4-trihydroxybenzo-phenones are normally reacted with reactive derivatives of (1,2-naphthoquinone 2-diazide)-4-sulfonic acid or of (7-methoxy-1,2-naphthoquinone 2-diazide)-4-sulfonic acid, in particular with the sulfonyl chlorides of the acids. The reaction is preferably carried out in inert solvents, such as ketones or chlorinated hydrocarbons, and in the presence of inorganic or organic bases, such as sodium carbonate or tertiary amines, for example triethylamine.

The (naphthoquinone diazide)sulfonic acid esters according to the invention may, however, also be prepared under phase transfer catalysis conditions, for example in a two-phase system composed of methylene chloride and an aqueous sodium carbonate or tetraalkylammonium hydroxide solution, using a suitable catalyst, such as tetrabutylammonium bromide.

The present invention furthermore relates to a radiation-sensitive mixture containing a water-insoluble polymeric binder which is, however, soluble, or at least swellable, in aqueous alkaline solutions and at least one radiation-sensitive compound, wherein the radiation-sensitive compound is one or more esters of the above-mentioned type.

The proportion of the radiation-sensitive compounds in the mixture according to the invention may be varied depending on need and is generally about 5 to about 40% by weight, preferably about 10 to about 35% by weight, particularly preferably about 15 to about 30% by weight, based in all cases on the total weight of the solids in the mixture according to the invention. The above percentages are for when the inventive compounds are used as the sole radiation-sensitive compound.

In addition to the (1,2-naphthoquinone 2-diazide)-4-sulfonic acid esters according to the invention, the mixture may also contain other radiation-sensitive components. Any known radiation-sensitive components can be used in any desired amount. When other radiation-sensitive components are used, the proportion of the esters according to the invention in the radiation-sensitive mixture may vary within wide limits. In some cases, even a small amount of esters according to the invention in a mixture along with other radiation-sensitive components is sufficient to impart a surprisingly higher solubility and shelf life in total to the radiation-sensitive component. In general, when used with other radiation-sensitive components the proportion of the esters according to the invention is about 5 to about 99% by weight, preferably about 20 to about 80% by weight, particularly preferably about 30 to about 70% by weight, based in all cases on the total weight of all of the radiation-sensitive components.

Especially suitable as further radiation-sensitive components are tri- or tetrahydroxybenzophenones completely or partly esterified with (naphtho-quinone diazide)sulfonic acid.

The radiation-sensitive mixtures according to the invention furthermore contain a polymeric, water-insoluble resinous binder which dissolves in the solvents used for the mixture according to the invention and is likewise soluble, or at least swellable, in aqueous alkalis. Any binder or mixture of binders having these characteristics can be used. The binder is used in an amount effective to accomplish the desired results.

The novolak condensation resins which have proved advantageous as binders in many positive copying materials have been found to be particularly useful and advantageous in the mixtures according to the invention. As a starting component for preparing the novolak, use may be made of phenols, cresols and xylenols, and alkylphenols in general. Aldehydes or ketones are the second component. The nature and proportion of the novolak resins in the mixture may vary with application purpose. In general, the proportion of novolak is between about 60 and about 95% by weight, preferably between about 65 and about 90% by weight, particularly preferably between about 70 and about 85% by weight, based in all cases on the total weight of the solid component in the mixture.

Polymeric compounds containing lateral hydroxyphenyl groups are likewise suitable as binders. These contain, in particular, monomer units composed of vinylphenols and esters and amides of acrylic acid and methacrylic acid with polyhydroxyl or aminohydroxyl aromatics, such as hydroquinone, pyrocatechol, resorcinol, pyrogallol and hydroxyaniline. In addition to the homopolymers, copolymers are also suitable. The copolymers may also contain further monomer units, for example those of styrene, methacrylic acid ester, acrylic acid ester, biphenylol methacrylate or biphenylol acrylate. Mixtures of these polymers with novolaks may also be used. The nature and proportion of the binders in the mixture may vary with application purpose, the proportion of total binders generally corresponding, however, to the proportion specified for the novolaks.

Furthermore, yet other substances, such as dyes, plasticizers, wetting agents, adhesion promoters, and the like may be added to the radiation-sensitive mixtures according to the invention to comply with specific requirements.

The mixture of the present invention may be used to coat a substrate, thereby producing a radiation-sensitive recording material. The mixture may be applied to the substrate in any desired manner. Any desired substrate may be used. For example, to coat a substrate material, for example, to produce the copying material according to the invention, the mixtures are generally dissolved in a solvent. The choice of the solvent should be matched to the planned coating process, the layer thickness, and the drying conditions. Suitable solvents are, in particular, ketones such as butanone, N-methylpyrrolidone, glycol monoethers, such as ethylene glycol monomethyl ether, propylene glycol monomethyl and monoethyl ether, glycol ether acetates such as ethylene glycol ethyl ether acetate and propylene glycol alkyl ether acetate, and esters such as butyl acetate. Solvent mixtures may also be used. The mixtures may also contain, in addition, aromatics such as xylene. In principle, all those solvents or mixtures thereof may be used which have an adequate solvent power and do not react irreversibly with the components of the layer.

The mixtures according to the invention can be used as radiation-sensitive components in copying materials, in particular in photoresists for the production of microchips. Preferred layer substrates are silicon wafers, which may also be superficially oxidized. Equally suitable are substrates composed of silicon nitride, polysilicon, silicon oxide, polyimides, or metals, such as aluminum, silicon doped with suitable materials, and wafers composed of Ga/As alloys.

The mixtures according to the invention may furthermore be used in manufacturing printed circuit boards. They can also be used to produce radiation-sensitive printing plates. In this case, suitable layer substrates are, in particular, aluminum sheets which have undergone a suitable pretreatment.

The layer substrates used in the microelectronics industry are advantageously coated by spinning-on of the radiation-sensitive mixture. However, other coating techniques, such as spraying, roller application, immersion, application by means of slot dies, doctor-blading or flow-coating may also be used.

During the development of the radiation-sensitive material, the regions of the radiation-sensitive layer affected by the radiation are removed, a positive image of the master being left behind. Any known developers can be used. Development is generally carried out in aqueous alkaline solutions. The latter may be free of metal ions but may also contain metal ions, such as sodium and/or potassium. The developer solutions may be buffered, for example with silicate, borate or phosphate solutions or suitable mixtures of salt solutions. Advantageously, they may also contain small amounts of surfactants.

With a suitable composition of the radiation-sensitive mixture, negative images may also be generated. For example, if the layer irradiated through a master is heated, if necessary while being gasified with an amine, then irradiated over the entire surface and only developed thereafter, then a negative image can be produced.

The radiation-sensitive mixtures according to the invention are preferably applied in the production of integrated circuits or of discrete components. In such cases, they act as masking material for various processing steps, such as etching the layer substrate, implanting ions in the layer substrate or depositing materials on the layer substrate.

The mixtures of the present invention are also useful in lithographic processes. Important lithographic assessment criteria are, inter alia, the resolution of a resist, i.e., the smallest patterns which can still be generated with a resist, the processing tolerance, i.e., the change in the pattern dimensions on changing the irradiation energy, and the radiation sensitivity, i.e., the irradiation energy which is necessary to reproduce the patterns of the mask master with dimensional fidelity by the lithographic process. For reproducible processing of the resist, it is important that, on the one hand, the lithographic characteristic values do not alter during the storage of the resist and also, on the other hand, no particles (crystals or gel particles) which would disturb the uniformity of the resist layer are deposited during storage. Such particles lead to defects in the resist layer, and this results in a reduction in the yield of the lithographic process. In addition, such particles often bring about blockages in the filters of the pumps which convey the resist to the coating machine, and this makes a more frequent filter replacement necessary.

The esters according to the invention result in mixtures which have at least equally as good lithographic properties as mixtures containing (naphthoquinone diazide) 4-sulfonic acid esters of unsubstituted 2,3,4-trihydroxy-benzophenone, but have a substantially improved shelf life.

Examples of mixtures according to the invention are described below. The examples do not restrict the inventive idea to said examples, but are merely exemplary of the present invention.

EXAMPLE 1 a) Preparation of 2,3,4-Trihydroxy-3'-methylbenzophenone 12.6 g of pyrogallol are added in portions to 13.6 g of 3-methylbenzoic acid in 14.4 ml of boron trifluoride etherate. The reaction mixture is heated for 2.5 h at 80° C., allowed to cool, 50 ml of water being added during cooling, and then extracted with methylene chloride. The organic phase is neutralized and dried. The solvent is then stripped. 13.1 g of 2,3,4-trihydroxy-3'-methylbenzophenone, which can be recrystallized from water, are left behind. It is obtained in the form of pale-yellow crystals having a melting point of 108.5° to 110° C. Analysis of the produced product is as follows.

| Combustion analysis: | % theoret. | % found |
|---|---|---|
| | C 68.85 | 68.7 |
| | H 4.95 | 4.9 |
| $^1$H-NMR (in DMSO-d$_6$): | 2.40 ppm | s, 3 H, —CH$_3$ |
| | 6.49 ppm | d, 1 H, aromatic proton in the trihydroxyphenyl group |
| | 6.99 ppm | d, 1 H, aromatic proton in the trihydroxyphenyl group |
| | 7.43 ppm | m, 4 H, aromatic protons in the tolyl group |

IR analysis (pressed KBr disc): 1632 cm$^{-1}$: C=O band b) Preparation of 2,3,4-Trihydroxy-3'-methylbenzophenone completely esterified with (1,2-naphthoquinone 2-diazide)-4-sulfonic acid 4.55 g of N-methylmorpholine are slowly added dropwise to 12.09 g of (1,2-naphthoquinone 2-diazide)-4-sulfonyl chloride and 3.66 g of 2,3,4-trihydroxy-3'-methylbenzophenone in 100 ml of acetonitrile. After 1.5 hours at room temperature, the reaction mixture is poured into 800 ml of 0.1N hydrochloric acid and the precipitate produced (8.8 g) is filtered off by suction. A yellow solid having a melting point of approx. 170° C. (with decomposition) is obtained (compound 1) having the following analysis.

| Combustion analysis: | isolated as the monohydrate | |
|---|---|---|
| | % theoret. | % found |
| | C 55.11 | 54.9 |
| | H 2.73 | 2.4 |
| | N 8.76 | 8.8 |
| | S 10.03 | 10.0 |
| UV analysis (in ethyl glycol acetate): $\lambda_{max}$ 378 nm | | |
| IR analysis (pressed KBr disc): | 1628 cm$^{-1}$ | C=O band |
| | 2145 cm$^{-1}$ | C=N=N band |

EXAMPLE 2 (compound 2)

Using the procedure as described under Example 1b, 2,3,4-trihydroxy-3'-methylbenzophenone is reacted with the three-fold molar amount of (7-methoxy-1,2-naphthoquinone 2-diazide)-4-sulfonyl chloride to form the corresponding completely esterified product.

EXAMPLE 3 (compound 3)

Using the procedure as described under Example 1b, 2,3,4-trihydroxy-3'-methylbenzophenone is reacted with the three-fold molar amount of a mixture of 0.9 parts by weight of (7-methoxy-1,2-naphthoquinone 2-diazide)-4-sulfonyl chloride and 0.1 part by weight of (1,2-naphthoquinone 2-diazide)-4-sulfonyl chloride to form the corresponding ester.

EXAMPLE 4 (compound 4)

Using the procedure as described under Example 1b, 0.5 parts by weight of 2,3,4-trihydroxy-3'-methylbenzophenone and 0.5 parts by weight of 2,3,4-trihydroxybenzophenone are reacted with the three-fold molar amount of a mixture of 0.9 parts by weight of (7-methoxy-1,2-naphthoquinone 2-diazide)-4-sulfonyl chloride and 0.1 part by weight of (1,2-naphthoquinone 2-diazide)- 4-sulfonyl chloride to form the corresponding fully esterified product.

COMPARISON EXAMPLE 1 (compound 5)

As described under Example 1b, 2,3,4-trihydroxybenzophenone is reacted with the three-fold molar amount of (1,2-naphthoquinone 2-diazide)-4-sulfonyl chloride to form the corresponding triester.

COMPARISON EXAMPLE 2 (compound 6)

As described under Example 1b, 2,3,4-trihydroxybenzophenone is reacted with the three-fold molar amount of (7-methoxy-1,2-naphthoquinone 2-diazide)- 4-sulfonyl chloride to form the corresponding triester.

COMPARISON EXAMPLE 3 (compound 7)

As described under Example 1b, 2,3,4-trihydroxybenzophenone is reacted with the three-fold molar amount of a mixture of 0.9 part by weight of (7-methoxy-1,2-naphthoquinone 2-diazide)-4-sulfonyl chloride and 0.1 part by weight of (1,2-naphthoquinone 2-diazide)- 4-sulfonyl chloride to form the corresponding triester.

COMPARISON EXAMPLE 4 (compound 8)

As described under Example 1b, 2,3,4-trihydroxy-3'-methyl-benzophenone is reacted with the three-fold molar amount of (1,2-naphthoquinone 2-diazide)-5-sulfonyl chloride to form the corresponding triester.

APPLICATION EXAMPLE 1 (solubility)

To compare the solubilities of compound 1 and compound 5, both compounds were prepared in crystalline form and saturated solutions in propylene glycol methyl ether acetate were then prepared therefrom. The content of the solutions is determined by UV spectroscopy by measuring the absorbance at $\lambda_{max}$ and comparing it with a calibration straight line obtained from solutions of known concentration. The solubility of compound 1 is 1.7% by weight and that of compound 5 only 0.4% by weight, and this implies an increase in solubility by a factor of 4.

APPLICATION EXAMPLE 2 (solubility)

To test the solubilities of compounds 2, 3, 4, 6, 7 and 8, saturated solutions of the naphthoquinone diazides in propylene glycol methyl ether acetate (PGMEA) containing 25% by weight of novolak are prepared. The solutions obtained in this way demonstrate the realistic conditions in a photoresist very well. The concentration of the saturated solution is determined by measuring the UV absorption at $\lambda_{max}$ and comparing it with a calibration straight line. The results are shown in Table 1.

TABLE 1

| Solubilities of the naphthoquinone diazides | |
|---|---|
| Compound | Solubility |
| 2 | >26.1% by weight |
| 3 | >27.9% by weight |
| 4 | >39.3% by weight |
| 6 | 6.5% by weight |
| 7 | 8.5% by weight |
| 8 | 3.3% by weight |

APPLICATION EXAMPLE 3 (shelf life and lithographic properties)

To determine the shelf life and the lithographic properties, a photoresist having the following formulation is prepared from the compounds according to the invention and the comparison compounds:

5.6 parts by weight of naphthoquinone diazide, 18.7 parts by weight of novolak (composed of m- and p-cresol and xylenols) having a mean molecular weight $M_w$ of 4200 (with a polystyrene standard as reference), 36.5 parts by weight of propylene glycol methyl ether acetate.

As a measure of the shelf life, use is made of the time which elapses before the naphthoquinone diazides start to crystallize from the resist solution, the resists being stored at room temperature. The results are listed in Table 2.

The radiation sensitivity (defined as the irradiation energy necessary to transfer the mask patterns to the resist) in relative units, the dark erosion (that is the resist eroded in the unirradiated regions during development), and the contrast value (as a measure of the dissolving power of the resists) are specified as lithographic properties in Table 2.

Table 2 also cites the values of the UV absorption of the resists at $\lambda_{max}$ normalized with respect to the layer thickness.

TABLE 2

| | Resist Properties | | | | |
|---|---|---|---|---|---|
| Compound No. | UV absorption* | Relative Radiation Sensitivity | Dark Erosion nm | Contrast Value | Shelf life (days) |
| 1 | 0.599 | 1.03 | 14 | 1.5 | 17 |
| 2 | 0.409 | 1.05 | 8 | 2.5 | >49 |
| 3 | 0.411 | 1.02 | 7 | 2.4 | >49 |
| 4 | 0.410 | 0.95 | 12 | 2.5 | >49 |
| 5 | 0.616 | 1.00 | 8 | 1.5 | 5 |
| 6 | 0.421 | 0.94 | 10 | 2.1 | 14 |
| 7 | 0.421 | 0.90 | 12 | 2.3 | 16 |

*$\lambda_{max}$

Table 2 clearly shows that the UV absorption, radiation sensitivity, dark erosion and contrast value of the naphthoquinone diazides according to the invention are virtually indistinguishable from those of the comparison compounds, whereas the shelf life of the naphthoquinone diazides according to the invention is appreciably improved.

What is claimed is:

1. A positive-working radiation-sensitive mixture consisting essentially of a polymeric, water-insoluble binder which is soluble, or at least swellable, in organic solvents and aqueous alkaline solutions; and at least one radiation-sensitive compound which is a 2,3,4-trihydroxy-3'-methyl-, -ethyl-, -propyl- or -isopropylbenzophenone which is completely esterified with (i) both (1,2-naphthoquinone 2-diazide)-4-sulfonic acid and (7-methoxy-1,2-naphthoquinone 2-diazide)-4-sulfonic acid, or (ii) (7-methoxy-1,2-naphthoquinone 2-diazide)-4-sulfonic acid.

2. A radiation-sensitive mixture as claimed in claim 1, wherein the compound is completely esterified with (7-methoxy-1,2-naphthoquinone-2-diazide)-4-sulfonic acid.

3. A radiation-sensitive mixture as claimed in claim 1, wherein the compound is esterified with both (1,2,-naphthoquinone 2-diazide)-4-sulfonic acid and with (7-methoxy-1,2-naphthoquinone-2-diazide)-4-sulfonic acid.

4. A radiation-sensitive mixture as claimed in claim 1, wherein the compound is a 2,3,4-trihydroxy-3'-methylbenzophenone which is completely esterified with at least one of (i) or (ii).

5. A radiation-sensitive mixture as claimed in claim 4, wherein the compound is completely esterified with (7-methoxy-1,2-naphthoquinone- 2-diazide)-4-sulfonic acid.

6. A radiation-sensitive mixture as claimed in claim 4, wherein the compound is esterified with both (1,2,-naphthoquinone 2-diazide)-4-sulfonic acid and with (7-methoxy-1,2-naphthoquinone-2-diazide)-4-sulfonic acid.

7. A radiation-sensitive mixture as claimed in claim 1, wherein the proportion of said radiation-sensitive compound is about 5 to about 40% by weight, based on the total weight of the solids in the mixture.

8. A radiation-sensitive mixture as claimed in claim 1, which further comprises a different radiation-sensitive compound.

9. A radiation-sensitive mixture as claimed in claim 8, comprising about 5 to about 99% by weight of the esterified benzophenone radiation-sensitive compounds.

10. A radiation-sensitive mixture as claimed in claim 8, comprising as the different radiation-sensitive compound a tri- or tetrahydroxybenzophenone completely or partially esterified with (napthoquinone diazide)sulfonic acid.

11. A radiation-sensitive mixture as claimed in claim 1, wherein the polymeric binder is a novolak.

12. A radiation-sensitive mixture as claimed in claim 11, wherein the novolak is present in about 60 to about 95% by weight of the total weight of the solid component in the mixture.

13. A radiation-sensitive mixture as claimed in claim 1, wherein the binder is a polymeric compound having lateral hydroxyphenyl groups.

14. A radiation-sensitive recording material comprising a substrate and a radiation-sensitive layer, wherein the layer comprises a radiation-sensitive mixture as claimed in claim 1.

15. A process of making a material as claimed in claim 14, comprising applying said mixture dissolved in a solvent to the substrate and removing the solvent.

* * * * *